United States Patent [19]

Yamagishi

[11] Patent Number: 5,383,231
[45] Date of Patent: Jan. 17, 1995

[54] METHOD AND APPARATUS FOR ACQUIRING X-RAY CT IMAGE IN HELICAL SCANNING MODE, UTILIZING ELECTROCARDIOGRAM

[75] Inventor: Ichiro Yamagishi, Tokyo, Japan
[73] Assignee: Kabushiki Kaisha Toshiba, Kanegawa, Japan
[21] Appl. No.: 862,634
[22] Filed: Apr. 3, 1992
[30] Foreign Application Priority Data
  Jun. 28, 1991 [JP] Japan .................................. 3-159075
[51] Int. Cl.6 ......................................... G01N 23/083
[52] U.S. Cl. ..................... 378/15; 378/901; 364/413.15; 364/413.16; 364/413.18; 364/413.19
[58] Field of Search ............................ 378/4, 15, 901; 364/413.15, 413.16, 413.17, 413.18, 413.19

[56] References Cited
U.S. PATENT DOCUMENTS

| | | | |
|---|---|---|---|
| 4,630,202 | 12/1986 | Mori | 364/414 |
| 4,994,965 | 2/1991 | Crawford et al. | 364/413.15 |
| 4,995,064 | 2/1991 | Wilson et al. | 378/99 |
| 5,262,946 | 11/1993 | Heuscher | 364/413.18 |
| 5,287,276 | 2/1994 | Crawford et al. | 364/413.19 |

Primary Examiner—Paul M. Dzierzynski
Assistant Examiner—David V. Bruce
Attorney, Agent, or Firm—Finnegan, Henderson Farabow, Garrett & Dunnar

[57] ABSTRACT

In a helical scanning type X-ray CT imaging system, a plurality of X-ray CT images of a biological body are reconstructed in synchronism with cardiac beats of a heart thereof to obtain such X-ray CT images free from image distortions. The helical scanning type X-ray CT imaging system comprises: an X-ray projection image data acquiring unit for acquiring continuous X-ray projection image data about a biological body under medical examination, while scanning both an X-ray source and an X-ray detector around the biological body in a helical scanning movement mode; an electrocardiogram data acquiring unit for acquiring a plurality of cardiac beats of a heart of the biological body as electrocardiogram data; a converting unit for converting temporal information contained in the electrocardiogram data into positional information of the biological body in connection with the helical scanning movement; and a reconstructing unit for reconstructing a plurality of X-ray CT images by processing the continuous X-ray projection image data based upon the positional information of the biological body, thereby producing the plural X-ray CT images having a specific relationship with phases of the cardiac beats of the heart.

17 Claims, 8 Drawing Sheets

METHOD AND APPARATUS FOR ACQUIRING X-RAY CT IMAGE IN HELICAL SCANNING MODE, UTILIZING ELECTROCARDIOGRAM

BACKGROUND OF THE INVENTION

1. Field of the Invention

The present invention generally relates to a method and an apparatus for acquiring X-ray CT images of a biological body under medical examination in a helical scanning mode. More specifically, the present invention is directed to such a method/apparatus that the X-ray CT (computerized tomographic) images of the biological body such as a heart of a patient is reconstructed in synchronism with an electrocardiogram of the biological body.

2. Description of Prior Art

Various types of X-ray CT imaging apparatus have widely been utilized in the medical examination field. When a heart and blood vessels of a biological body under examination are medically examined by employing such X-ray CT imaging apparatuses, a plurality of tomographic image data thereof are continuously produced, and then either a three-dimensional surface image or an MPR (multi-planar reconstruction) image is produced based upon the plural pieces of tomographic image data.

In accordance with one conventional X-ray imaging system, the scanning operation is performed in such a manner that a couch on which a patient (i.e., biological body under medical examination) is set, is intermittently translated along its longitudinal direction every time a single piece of tomographic image data is acquired, while interruptedly projecting X-ray beams to the patient. As a consequence, a lengthy X-ray CT imaging time is necessarily required so as to obtain not only X-ray CT images, but also such a three-dimensional surface image and an MPR image.

Figure 1:
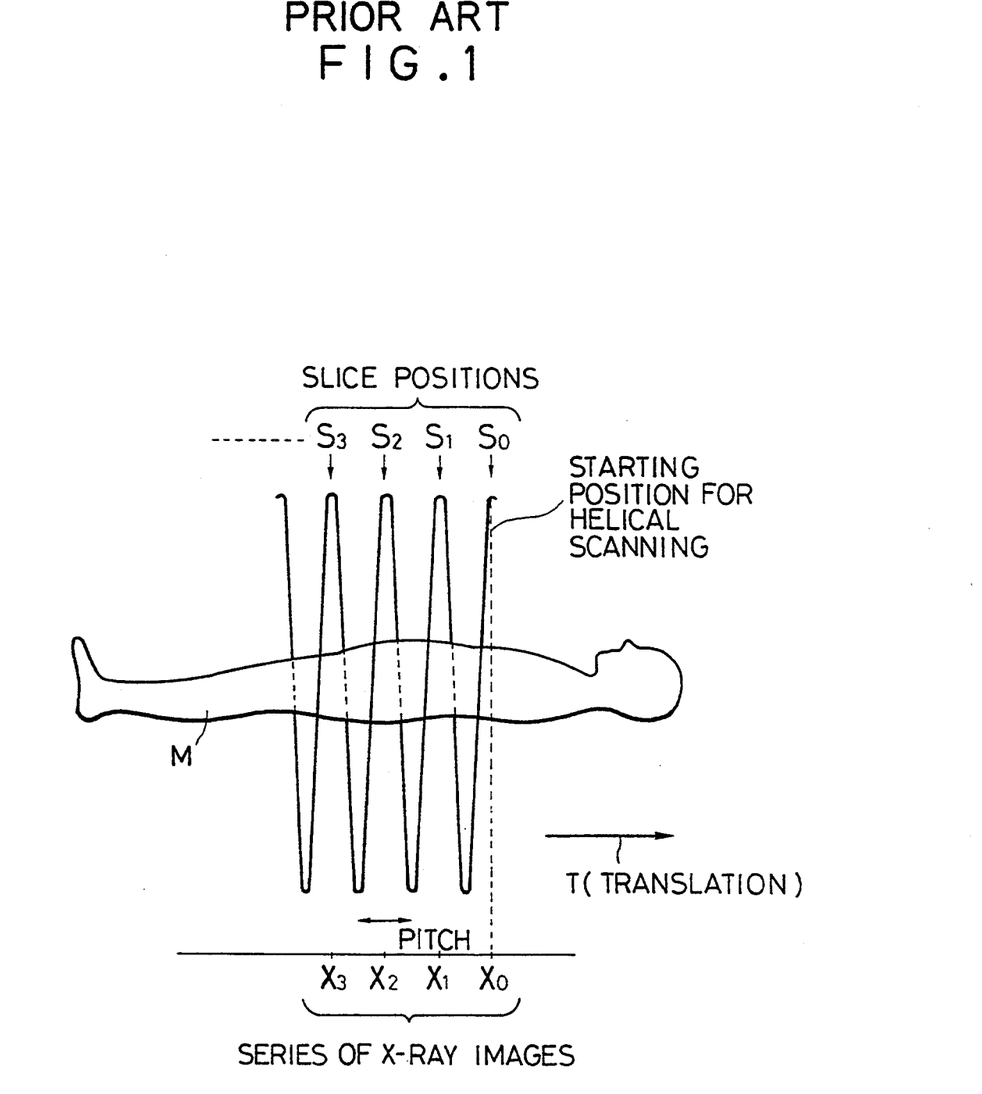
FIG. 1 schematically illustrates a basic idea of the known helical scanning operation employed in X-ray CT imaging systems.

To avoid such a lengthy X-ray image acquiring/processing operation, another X-ray imaging system so-called as "a helical scanning system" has been utilized in which while X-ray beams are continuously projected to the patient and a couch is also continuously translated along a longitudinal direction thereof. As a result, an organ of the patient, for instance, a heart and blood vessels can be medically examined at a higher speed than in the first-mentioned conventional X-ray CT imaging system. The helical scanning type X-ray imaging system is known from, for instance, U.S. Pat. No. 4,630,202, entitled "COMPUTERIZED TOMOGRAPHIC APPARATUS UTILIZING A RADIATION SOURCE" issued to Mori, on Dec. 16, 1986. In this helical scanning type X-ray imaging system, as represented in FIG. 1, a circumference of a patient "M" is continuously scanned by an X-ray detector unit (not shown in detail) and an X-ray source (not shown either) in a helical scanning mode, while a couch (not shown) on which the patent is laid is continuously translated along a direction indicated by "T ", whereby X-ray projection data "$S_0$" to "$S_3$" on the patient "M" are acquired and three-dimensional CT images thereof can be finally obtained by processing these X-ray projection data.

Very recently, such an idea has been developed in the helical scanning type X-ray imaging system that an X-ray contrast medium had been injected into the patient "M" prior to a commencement of a helical scanning operation in order to improve contrast effects of blood vessels in the X-ray images.

However, there are problems in the above-described conventional X-ray CT imaging systems that although a stationary portion of the patient "M" can be imaged with medical and photographic satisfaction, a moving imaging portion thereof such as a heart cannot be imaged as a series of "still" X-ray images. That is, a plurality of tomographic images which have been continuously acquired in the helical scanning mode, are obtained as not still images, but images containing motion artifacts. As a consequence, in particular, when a living heart of the patient "M" is medically examined by employing such a conventional helical scanning type X-ray CT imaging apparatus, it is practically difficult to acquire three-dimensional "still" images of this living heart, namely three-dimensional images containing motion artifacts.

As previously described, these conventional x-ray imaging systems have the following drawbacks. That is, since a lengthy X-ray examination time is required, various medical problems such as pain are given to patients. Moreover, even when the highspeed helical scanning type X-ray CT imaging systems are employed, a series of X-ray still images about a moving organ of a patient can be hardly acquired. Thus, the resultant three-dimensional images contain motion artifact components, resulting deterioration of image qualities thereof.

The present invention has been made in an attempt to solve the above-described various problems, and therefore has an object to provide a method capable of reconstructing X-ray CT images of a living organ of a biological body in synchronism with an electrocardiogram of this biological, thereby obtaining three-dimensional images thereof free from motion artifacts.

Another object of the present invention is to provide a helical scanning type X-ray imaging apparatus capable of obtaining three-dimensional X-ray images of a moving organ such as a heart of a patient from a series of X-ray still images thereof.

SUMMARY OF THE INVENTION

To achieve the above-described objects of the present invention, a method for reconstructing an X-ray CT (computerized tomographic) image of a biological body (20) under medical examination, comprises the steps of:

acquiring continuous X-ray projection image data of the biological body (20) under medical examination by scanning both an X-ray source (1:50) and an X-ray detector (2) around the biological body (20) in a helical scanning movement mode;

acquiring a plurality of cardiac beats of heart (22) of the biological body (20) as electrocardiogram data;

converting temporal information contained in the electrocardiogram data into positional information of the biological body (20) in connection with the helical scanning movement; and reconstructing a plurality of X-ray CT images by processing the continuous X-ray projection image data based upon the positional information of the biological body (20), thereby producing the plural X-ray CT images having a specific relationship with phases of the cardiac beats of the heart (22).

Furthermore, a helical scanning type X-ray imaging apparatus, according to the present invention, comprises:

X-ray projection image data acquiring means (1:2:3:9) for acquiring continuous X-ray projection image data about a biological body (20) under medical examination, while scanning both an X-ray source (1:50) and an X-ray detector (2) around the biological body (1) in a helical scanning movement mode;

electrocardiogram data acquiring means (10:11:12) for acquiring a plurality of cardiac beats of a heart (22) of the biological body (20) as electrocardiogram data;

converting means (14) for converting temporal information contained in the electrocardiogram data into positional information of the biological body (20) in connection with the helical scanning movement; and reconstructing means (13) for reconstructing a plurality of X-ray CT images by processing the continuous X-ray projection image data based upon the positional information of the biological body (20), thereby producing the plural X-ray CT images having a specific relationship with phases of the cardiac beats of the heart (22).

BRIEF DESCRIPTION OF THE DRAWINGS

The above purposes and other useful features of the present invention will become more readily apparent from the following description in conjunction with the accompanying drawings, in which.

DETAILED DESCRIPTION OF THE PREFERRED EMBODIMENTS

Basic Idea

Before describing various preferred embodiments, a basic idea of the present invention will now be summarized.

In an X-ray CT (computerized tomographic) imaging system, electrocardiogram data are acquired while scanning a biological body under medical examination such as a patient in the helical scanning mode, thereby to also acquire continuous X-ray projection image data. Thereafter, a selection is made of only a series of X-ray projection data acquired at a specific phase of the cardiac beats, for instance, a central time instant within an expansion period. Then, X-ray CT images free from image distortions are reconstructed from these selected projection image data in synchronism with the cardiac beats, or electrocardiograms. Finally, desirable three-dimensional images such as surface images are produced based on these X-ray CT images free from image distortions.

Overall Arrangement of Helical Scanning Type X-ray C Imaging System

Figure 2:
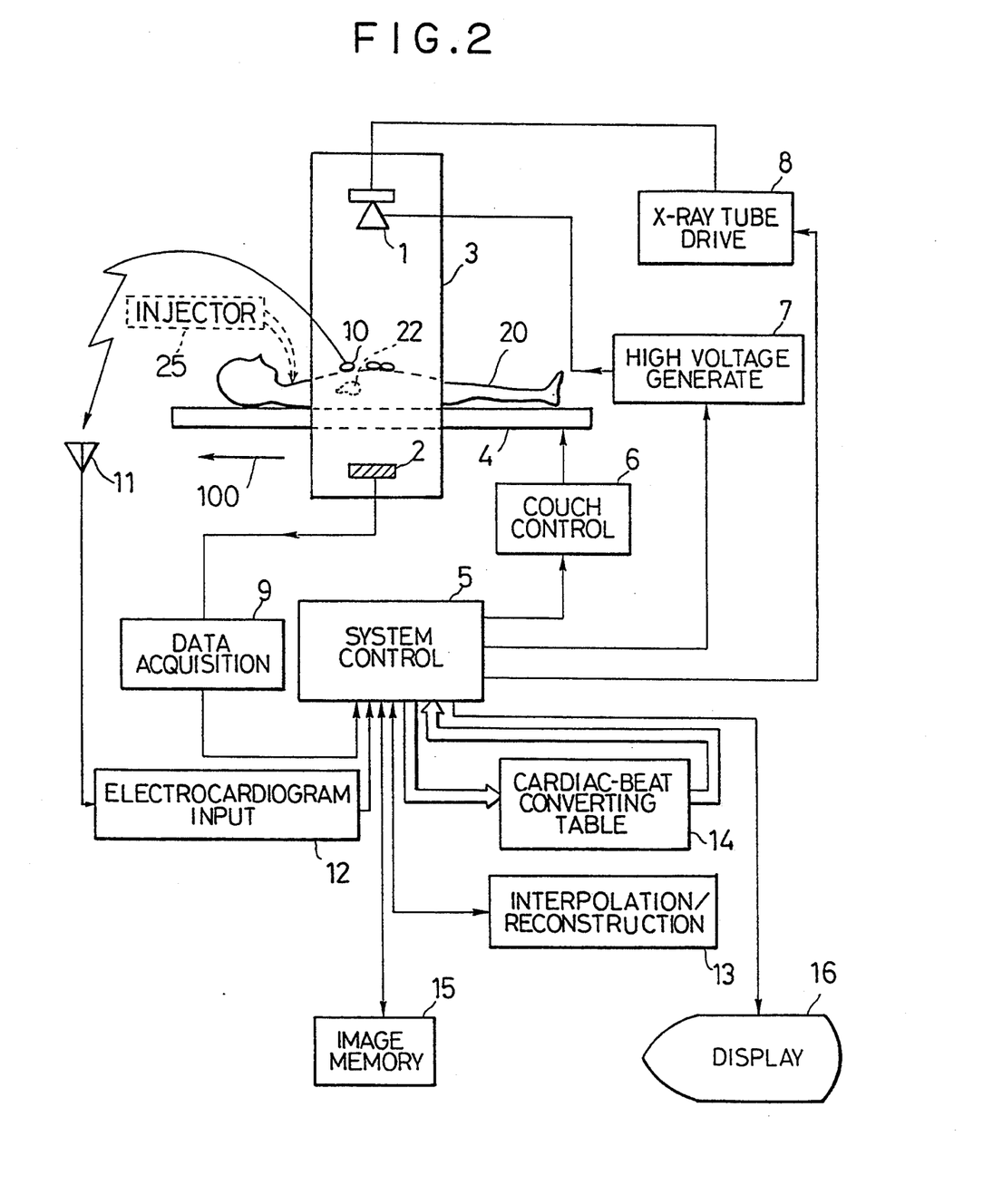
FIG. 2 is a schematic block diagram for showing an overall arrangement of a helical scanning type X-ray CT imaging system according to a preferred embodiment of the present invention.

Referring now to FIG. 2, an overall arrangement of a helical scanning type X-ray CT (computerized tomographic) imaging system according to a preferred embodiment of the present invention will be described.

The helical scanning type X-ray CT imaging system comprises an X-ray tube 1 and a single X-ray detector 2 both mounted on a gantry 3, through which a couch 4 is translatable along a longitudinal direction 100 in the continuous drive mode (will be discussed later) to achieve the helical scanning operation. A biological body under medical examination is such as a patient 20 having a heart 22. This CT imaging system further includes a system control unit 5 for controlling an overall system; a couch drive controlling unit 6 for controlling a translation drive of the couch 4; a high-voltage generating unit 7 for generating a high voltage required to energize the X-ray tube 1; and an X-ray tube drive controlling unit 8 for controlling a helical drive of the X-ray tube 1. Under control of the system control unit 5, while both the X-ray tube 1 and the X-ray detector 2 are rotated at a high speed by the X-ray tube drive controlling unit 8 under condition that the high voltage is being applied to the X-ray tube 1 from the high voltage generating unit 7, in order to achieve a high-speed continuous scanning operation, the couch 4 on which the patient 20 is laid is translated in the continuous mode along the longitudinal direction 100, whereby the helical scanning operation can be realized. It should be noted that a couch having a structure of fourth generation may be employed as this couch 4, in which a slip ring (not shown) is utilized to achieve the continuous X-ray projection.

To the contrary, in the conventional helical scanning system, the positional information about the couch is acquired and then stored into a predetermined memory region of a memory table (not shown) during the helical scanning operation. When the X-ray images are reconstructed, the specific positional information of this couch is read out from the memory table, and then the desirable tomographic images at a predetermined slice position are reconstructed based upon the continuous projection data corresponding to this slice position. This implies that these conventional tomographic images are obtained irrelevant to cardiac movement of a heart, or blood vessels of a patient. As a result, the three-dimensional surface images as well as the multi-planer slice images produced from these tomographich images contain three-dimensional image distortions, which may deteriorate diagnoses with employment of the above-described three-dimensional images.

The present invention has been made in an attempt to solve the above-described various problems, and therefore has an object to provide a method capable of reconstructing X-ray CT images of a living organ of a biological body in synchronism with an electrocardiogram of this bilogical, thereby obtaining three-dimensional images thereof free from motion artifacts.

Thus, continuous X-ray projection data are detected by the X-ray detector 2 during the high-speed helical scanning operation by these couch controlling unit 6, high voltage generating unit 7 and X-ray tube drive controlling unit 8. Then, the continuous X-ray projection data are acquired in a data acquiring unit 9 and supplied to the system control unit 5.

On the other hand, an electrode 10 having a transmitting function of electrocardiograms is attached on a skin of the patient 20 near a heart 22, whereby cardiac beats of this heart 22 can be transmitted from the electrode 10 via an antenna 11 to an electrocardiogram input unit 12. Accordingly, electrocardiogram data are supplied to the system control unit 5.

It should be noted that such an electrocardiogram data acquisition is executed indenpendently from the helical scanning operation, namely not in synchronism with the helical scanning operation.

This X-ray CT imaging system shown in FIG. 2 further comprises a data interpolation/reconstruction unit 13; a cardiac-beat converting table unit 14, and image data storage unit 15 and a display unit 16. It should be noted that since both the cardiac-beat converting table unit 14 and the data interpolation/reconstruction unit 13 constitute the major feature of the present invention, a detailed function thereof will be described later.

Roughly speaking, this X-ray CT imaging system is characterized in that temporal information is derived from the electrocardiogram data by the electrocardiogram input unit 12; this temporal information is converted into positional information of the couch 4 (namely, the patient 20) by the cardiac-beat converting table unit 14; and then the above-described continous X-ray projection data are interpolated/reconstructed based upon the positional information of the couch 4, whereby X-ray CT (computerized tomographic) image data free from image distortion can be produced, and therefore, desirable three-dimensional images such as MPR (Multi-Planar Reconstruction) images may be obtained with better image qualities (i.e., distortion-free images).

Detailed Functions Of Cardiac-Beat Converting Table Unit

Figure 3:
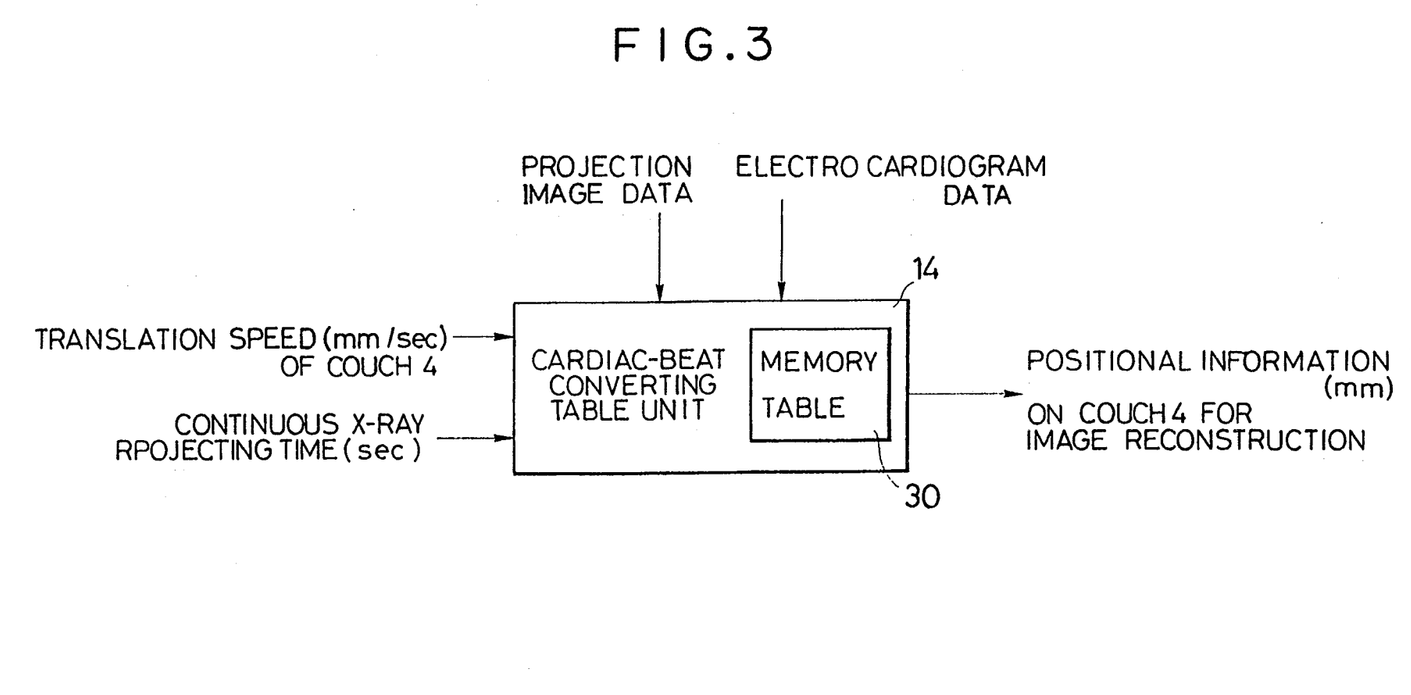
FIG. 3 schematically represents in detail, the cardiac-beat converting table unit 14 employed in the X-ray CT imaging system shown in FIG. 2.
Figure 4:
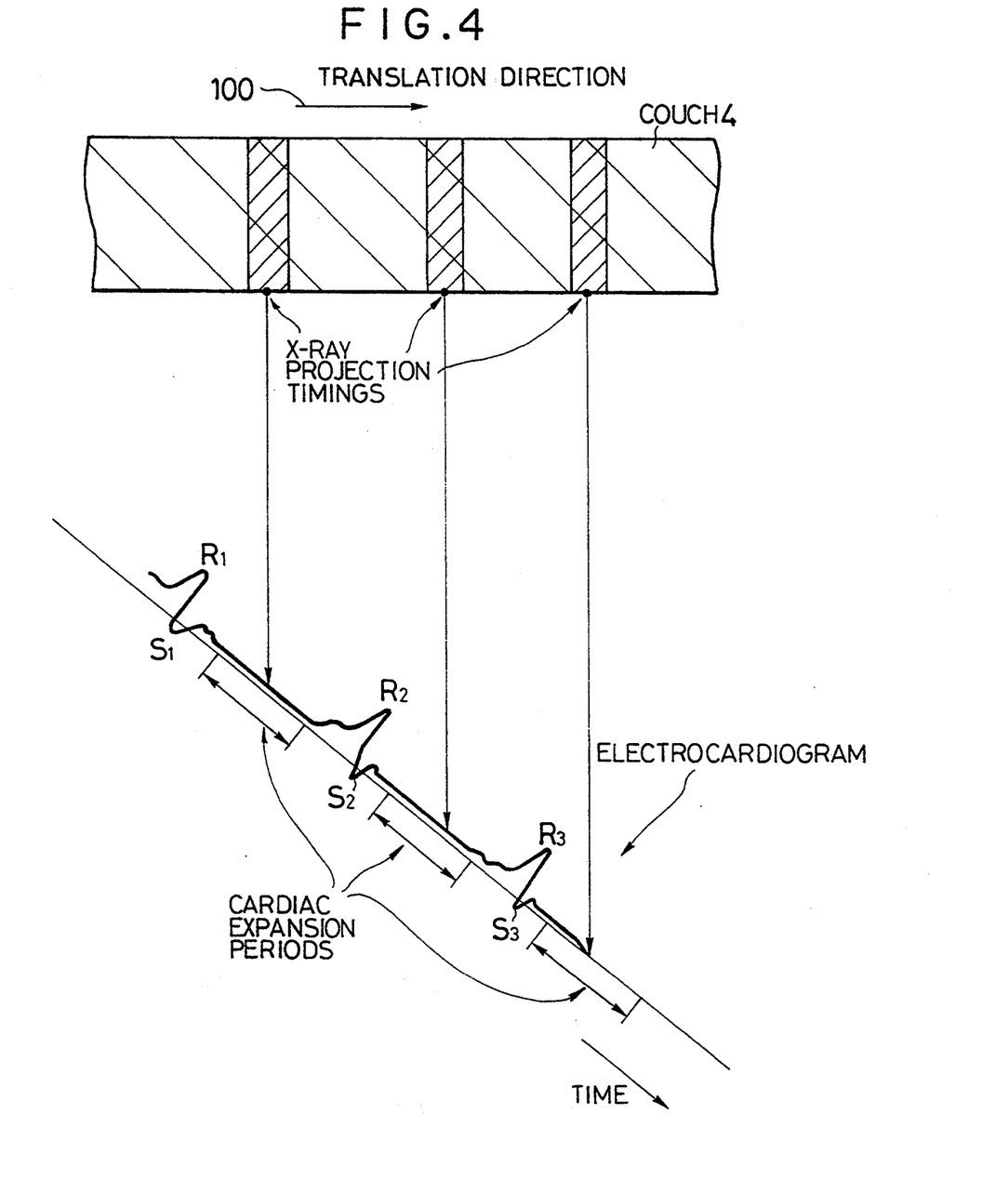
FIG. 4 pictorially explains projection-data acquisition timing in connection with the electrocardiograms in the X-ray CT imaging system of FIG. 2.

Referring now to FIGS. 3 and 4, various functions of the cardiac-beat converting table unit 14 will be described in detail.

To this cardiac-beat converting table unit 14, various data are inputted via the system control unit 5 from various units. These data are the X-ray projection data, electrocardiogram data, translation speed data (mm/sec) of the couch 4, and continuous X-ray projecting time data (sec). Then, these data are processed in this cardiac-beat converting table unit 14, and the above-described positional information data (mm) about the couch 4 are outputted therefrom for the image reconstruction purpose.

Precisely speaking, a relationship between the electrocardiogram data and the continuous projection data is as follows. A single piece of each relevant projection data among the acquired continuous X-ray projection data is previously stored as a peak (crest) value of an electrocardiogram measured at the same time instant where this projection data is acquired. That is to say, the electrocardiogram data, the continuous X-ray projection data, the translation speed data (1mm/sec) of the couch 4 and the continuous X-ray projecting time data (sec) are supplied from the system control unit 5 into this cardiac-beat converting table unit 14. Thereafter, for instance, central time instances within the cardiac expansion periods defined between the successive R-waves $R_1$, $R_2$, $R_3$ ... $R_n$, of the cardiac beats are calculated, namely the cardiac beats are obtained at the same phase within the cardiac expansion periods as represented in FIG. 4, based upon the above-described various data, and thereafter the resultant temporal data are converted into coordinate values in a longitudinal direction of the couch 4 or patient 20 (i.e., positions of the couch 4). In one practical method, these central time instants within the respective cardiac expansion periods are previously obtained by processing the actual time intervals between the sucessive R-waves $R_1$, $R_2$, $R_3$, ... $R_n$.

As previously described, the temporal information contained in the electrocardiogram data is converted into the positional information about the couch 4 by utilizing a memory table 30 employed in the cardiac-beat converting table unit 14 (see FIG. 3). Finally, the resultant positional information on the couch 4, namely the slice position data are supplied via the system control unit 5 to the interpolation/reconstruction unit 13.

Subsequently, in the interpolation/reconstruction unit 13, X-ray tomographic image data are reconstructed by processing these X-ray projection image data in conjunction with the positional information about the couch 4 (namely, slice position data) obtained from the cardiac-beat converting table unit 14. Accordingly, desirable three-dimensional images such as surface images and MPR images can be produced without any image distortions by interpolating these X-ray tomographic image data, and will be displayed on the display unit 16 in the helical scanning type X-ray imaging system shown in FIG. 2.

Figure 5:
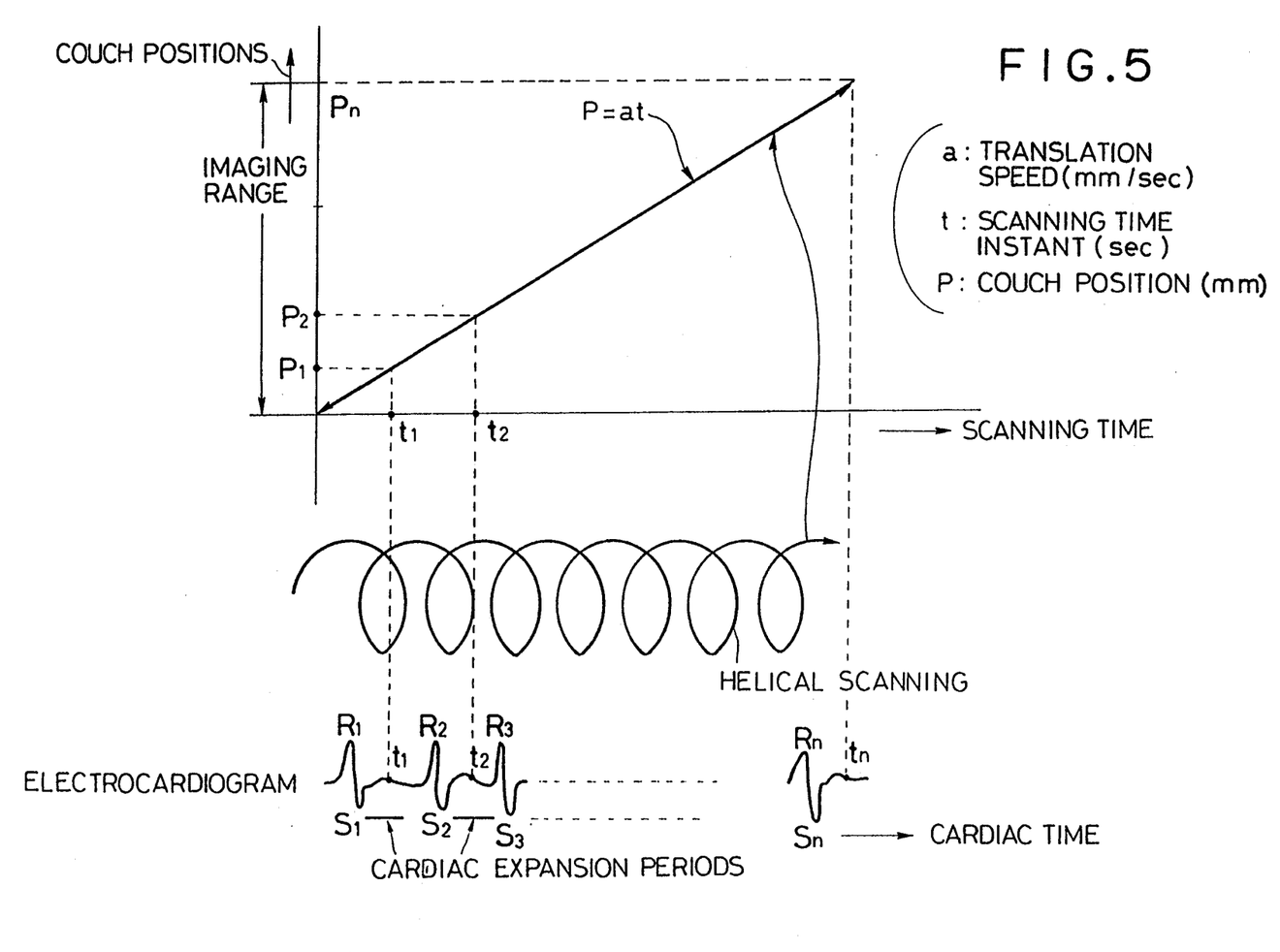
FIG. 5 is an illustration for explaining contents of the cardiac-beat converting table unit 14 shown in FIG. 3.

Pictorial Explanations of Image Data Acquisition Timings Cardiac-Beat Converting FIG. 5 pictorically explains both X-ray projection data acquisition timings and cardiac beat conversion.

As apparent from FIG. 5, data acquisition timings $t_1$, $t_2$, ... $t_n$ are set to a central time instant within each of the cardiac expansion periods in the electrocardiogram, at which X-ray tomographic images are reconstructed. Also, each of the couch positions $P_1$, $P_2$, ... $P_n$ may be calculated from the following equation (1):

$$p = a \cdot t \qquad (1),$$

where symbol "P" denotes a present position of the couch 4, symbol "a" indicates a translation speed (mm/sec) of the couch 4, and symbol "t" represents a scanning time instant. As a result, for instance, one present position "$P_2$" of the couch 4 may be calculated as follows:

$$P_2 = a \cdot t_2 \qquad (2).$$

As obvious from these pictorial explanations, the positional data $P_1$, $P_2$, ..., $P_n$ of the couch 4 may be simply obtained by conversion-processing the central time instants $t_1$, $t_2$, ..., $t_n$ of the cardiac expansion periods, namely at the same phases of the respective cardiac beats.

Overall Flow Operation of Helical Scanning Type X-Ray CT Imaging System

Figures 6, 6A:
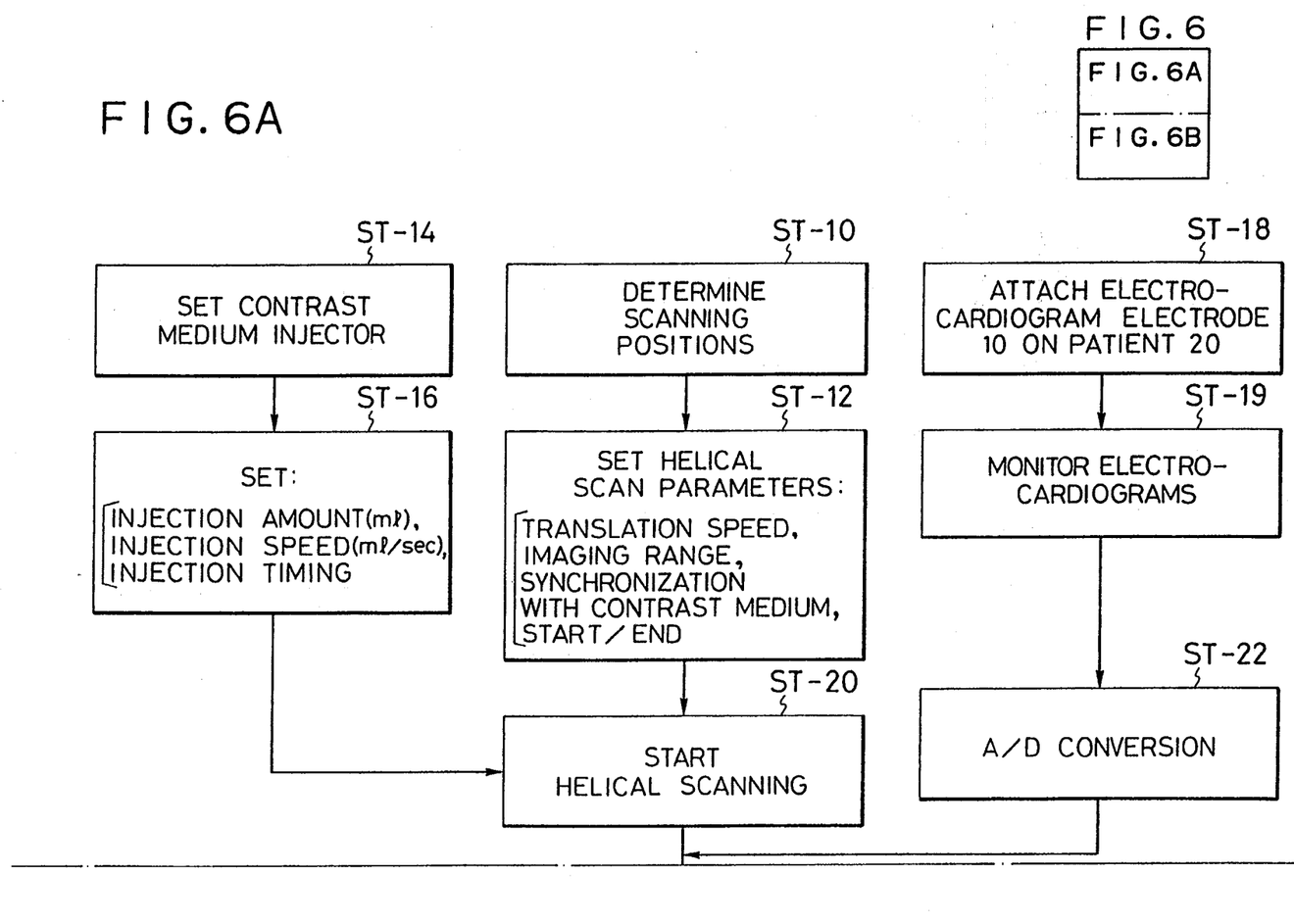
FIGS. 6, 6A and 6B illustrate a flow chart for explaining an overall operation of the helical scanning type X-ray CT imaging system shown in FIG. 2.

FIG. 6 is a flow chart for explaining an overall operation of the helical scanning type X-ray CT imaging system shown in FIG. 2, for a better understanding of especially the cardiac-beat/couch position converting operation effected in the cardiac-beat converting table unit 14 functioning as the major feature of the present invention.

In the flow chart shown in FIG. 6A, first, scanning positions of the patient 20 (see FIG. 2) are determined at a step ST-10. At a next step ST-12, various parameters (see FIG. 6) are set as helical scanning conditions.

On the other hand, an X-ray contrast medium injector 30 shown in FIG. 2 is set at a step ST-14. Thereafter, an injection amount (ml) of the contrast medium, an injection speed (ml/sec) thereof and an injection timing thereof are set at a step ST-16 for the helical scanning purpose.

Furthermore, the electrode 10 is attached to the skin of the patient 20 near the heart 22 so as to transmit the cardiac beats to the antenna 11 of the electrocardiogram input unit 12 at a step 18. Then, the electrocardiograms of the patient 20 are monitored on the display unit 16 at a step 19.

Figure 6B:
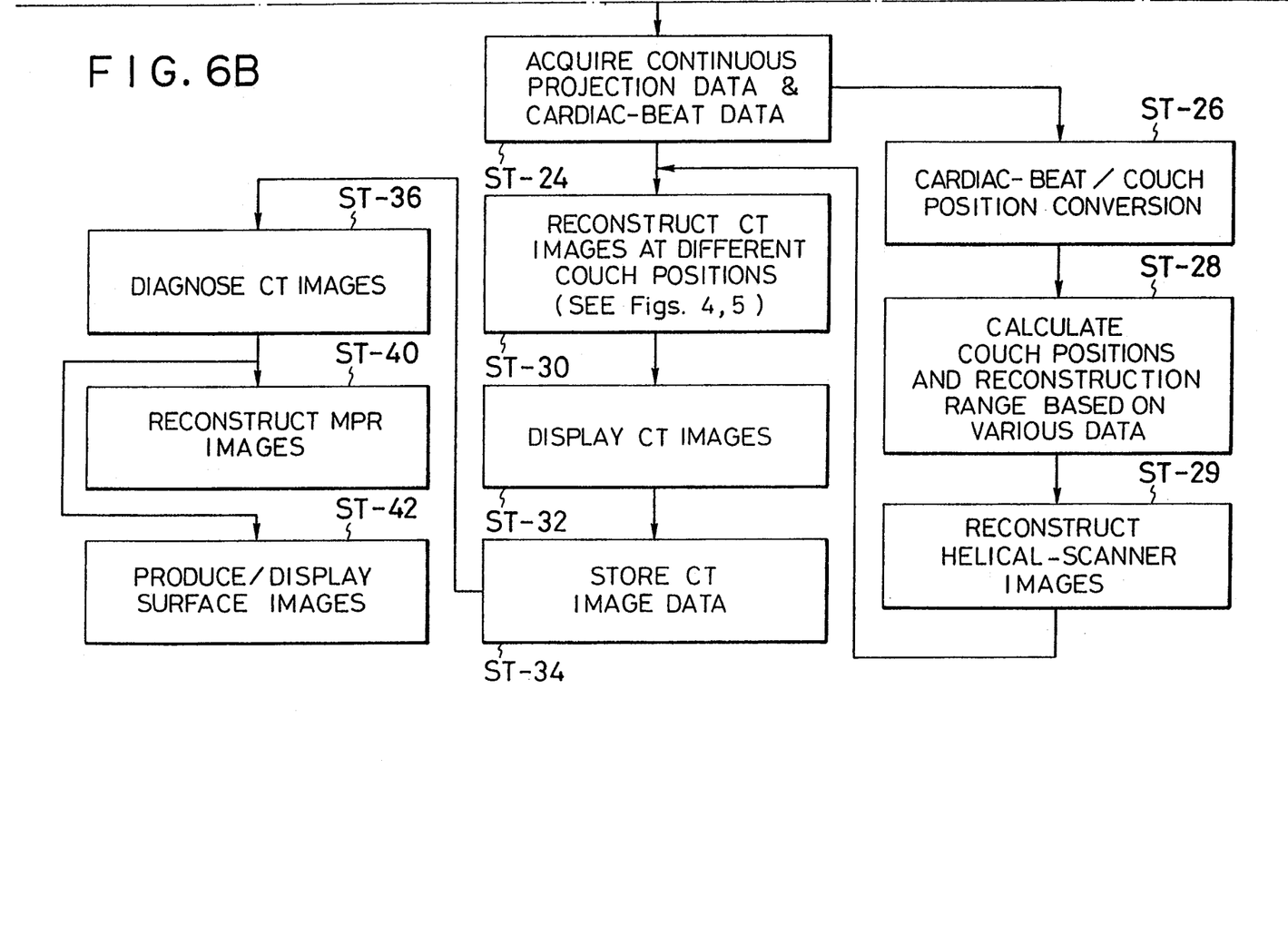

Subsequently, under the above-described present conditions, the helical scanning operation of the X-ray CT imaging system is commenced at a step ST-20. The electrocardiogram signals monitored on the display unit at the previous step ST-19, are A/D-converted into corresponding digital electrocardiogram data at a step ST-22 which will be utilized in the next step ST-24. At this step ST-24 as shown in FIG. 6B, the continuous X-ray projection data are acquired in the helical scanning type X-ray CT imaging system represented in FIG. 2, and also the cardiac-beat data (electrocardiogram data) are similarly acquired from the electrode 10, antenna 11 and electrocardiogram input unit 12.

After such data acquisition operations, the acquired cardiac-beat data are converted into corresponding positional data of the couch 4 by the cardiac-beat converting table unit 14 at a step ST-26. Then, the positions of the couch 4 and the reconstruction (imaging) range are obtained based on the couch translation speed, cardiac-beat data, scanning time (center time instants within cardiac expansion periods) at a subsequent step ST-28. Thereafter, the helical-scanned images are reconstructed at a step ST-29.

At a step 30, tomographic images are reconstructed from the acquired X-ray projection data at the different couch positions (namely, in the same phases within the different cardiac expansion periods as shown in FIGS. 4 and 5). In other words, these CT images are reconstructed in synchronism with the cardiac beats of the heart 22 of the patient 20. Next, these CT images are displayed on the display unit 16 at a step ST-32. Then, these CT image data are stored in the image memory 15 at a step ST-34.

At a subsequent step ST-36, these CT image data are read out from the image memory 15 so as to diagnose the CT images about the heart 22 of the patient 20.

On the other hand, MPR (Multi-Planar Reconstruction) images are reconstructed in the interpolation/reconstruction unit 13 under control of the system control unit 5 based on the reconstructed CT images at a step ST-40, and/or three-dimensional surface images are produced therein and then displayed on the display unit 16 at a step 42.

Modification

Figure 7:
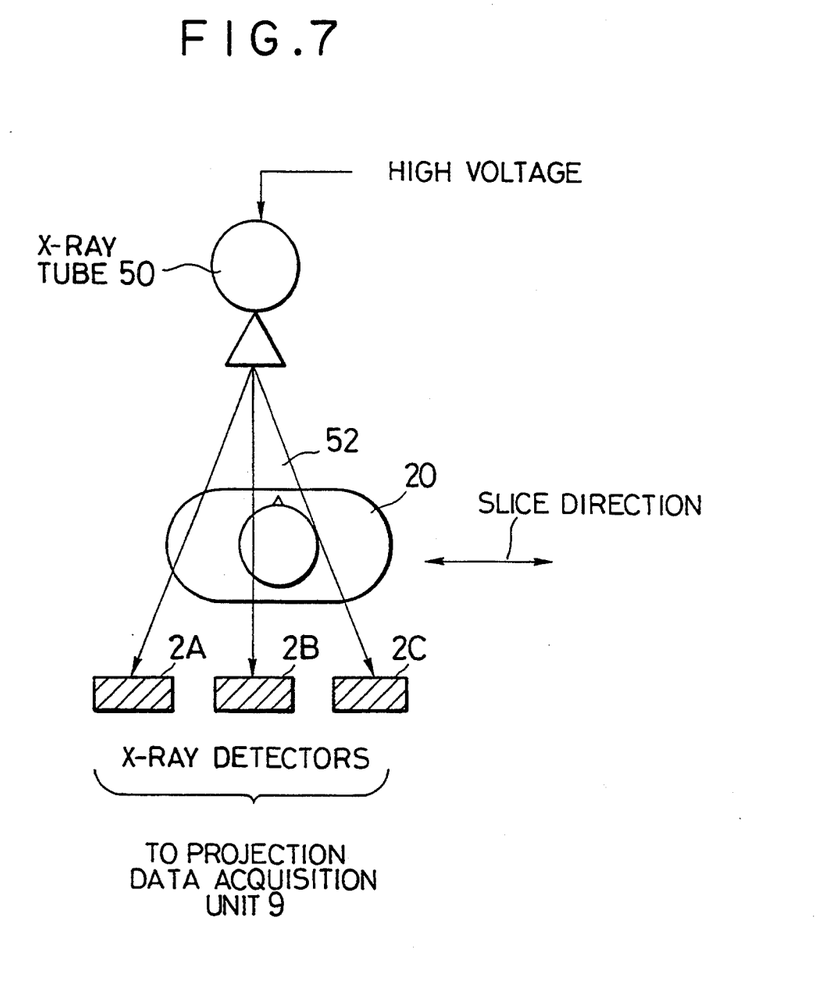
FIG. 7 pictorially shows X-ray tube/X-ray detectors employed in a volumetry X-ray CT imaging system according to a modification of the present invention.

In the above-described helical scanning type X-ray CT imaging system shown in FIG. 2, only a single X-ray tube 1 and a single X-ray detector 2 are mounted on the gantry 3, and are relatively rotated around the patient 20. However, the above-described image reconstructing operation in synchronism with the cardiac beats according to the present invention is not limited to such a helical scanning type system, but may be applied to other scanning systems. For instance, as illustrated in FIG. 7, only one X-ray tube 50 is similarly employed, and at least three X-ray detectors 2A, 2B and 2C are arranged along a slice direction in a so-called volumetry X-ray CT imaging system, to which the inventive idea of the present invention may be also applied. It should be noted that X-ray beams 52 having a certain width along the slice direction are emitted from this X-ray tube 1.

As previously described in detail, the helical scanning type X-ray CT imaging system of the present invention has such particular advantages that since a plurality of X-ray projection image data are quickly acquired in the continuous mode by way of the helical scanning method, a total time period for the image data acquisition can be shortened, as compared with that of the conventional X-ray CT imaging system. Accordingly, a total amount of the X-ray contrast medium can be reduced, as compared with that of the conventional X-ray CT imaging system, whereby any patients do not feel pain during the medical examination by this helical scanning type X-ray CT imaging system.

Moreover, in accordance with the present invention, since a plurality of X-ray CT images are reconstructed in synchronism with cardiac beats of a heart of a patient, three-dimensional images (MPR images, surface images) of this heart free from image distortions, or motion artifacts can be produced.

What is claimed is:

1. A method for reconstructing an X-ray CT (computerized tomographic) image of a biological body under medical examination, the method comprising the steps of:

acquiring continuous X-ray projection data of the biological body under medical examination by scanning an X-ray source around the biological body in a helical scanning movement mode;

acquiring a plurality of cardiac beats of a heart of the biological body as electrocardiogram data independent of the projection data acquiring step;

converting temporal information contained in the electrocardiogram data into positional information of the biological body in connection with the helical scanning movement mode;

determining a specific phase of the electrocardiogram data; and reconstructing a plurality of X-ray CT images by processing the continuous X-ray projection data based upon the positional information of the biological body obtained by the converting step, whereby the plurality of X-ray images are produced at the specific phases of cardiac beats of the heart determined by the determining step.

2. An X-ray CT imaging method as claimed in 1, further comprising the step of:

producing a three-dimensional image of the biological body by processing the plurality of X-ray CT images having a specific relationship with phases of the cardiac beats of the heart.

3. An X-ray CT imaging method as claimed in claim 2, wherein said plurality of X-ray CT images having a specific relationship with phases of the cardiac beats of the biological body are interpolated with each other to obtain one of an MPR (multi-planar reconstruction) image and a surface image of the biological body.

4. An X-ray CT imaging method as claimed in claim 1, wherein each of said phases of the cardiac beats of the heart are determined to be a substantially central time instant within a cardiac expansion period.

5. An X-ray CT imaging method as claimed in claim 1, further comprising the steps of:
injecting an X-ray contrast medium into the biological body, while performing the helical scanning movement, whereby a plurality of X-ray CT contrast images of the biological body are reconstructed.

6. An X-ray CT imaging method as claim in claim 1, wherein said X-ray source emits X-ray beams extending along a sectional direction of the biological body, and a plurality of X-ray detectors are arranged along the sectional direction in such a manner that all of said X-ray detectors can detect said X-ray beams extending along the sectional direction and passing through the biological body.

7. An X-ray CT (computerized tomographic) imaging system comprising:
X-ray projection data acquiring means for acquiring continuous X-ray projection data about a biological body under medical examination, while scanning an X-ray source around the biological body in a helical scanning movement mode;
electrocardiogram data acquiring means for acquiring a plurality of cardiac beats of a heart of the biological body as electrocardiogram data, wherein the X-ray projection data acquiring means and the electrocardiogram data acquiring means operate independently from each other;
converting means for converting temporal information contained in the electrocardiogram data into positional information of the biological body in connection with the helical scanning movement;
phase determining means for determining a specific phase of electrocardiogram data; and
reconstructing means for reconstructing a plurality of X-ray images by processing the continuous X-ray projection data based upon the positional information of the biological body obtained from the converting means, whereby the plurality of X-ray images are produced at the specific phases of cardiac beats of the heart determined by the phase determining means.

8. An X-ray CT imaging system as claimed in claim 7, further comprising:
means for producing a three-dimensional image of the biological body by processing said plurality of X-ray CT images having specific relationship with phases of the cardiac beats of the heart.

9. An X-ray CT imaging system as claimed in claim 8, wherein said three-dimensional image producing means interpolates said plurality of X-ray CT images having a specific relationship with phases of the cardiac beats of the heart so as to obtain said three-dimensional image.

10. An X-ray CT imaging system as claimed in claim 7, wherein each of the phases of the cardiac beats of the heart are determined to be substantially central time instants within cardiac expansion periods.

11. An X-ray CT imaging system as claimed in claim 7, wherein said converting means includes at least a memory table for previously storing a conversion table by which the temporal information contained in the electrocardiogram data is converted into the positional information about the biological body in connection with the helical scanning movement.

12. An X-ray CT imaging system as claimed in claim 7, further comprising:
injecting means for injecting an X-ray contrast medium into the biological body while performing the helical scanning movement, whereby a plurality of x-ray CT contrast images of the biological body are reconstructed.

13. An X-ray CT imaging system as claimed in claim 7, wherein said X-ray projection image data acquiring means includes:
a single X-ray tube for emitting X-ray beams extending along a sectional direction of the biological body; and
a plurality of X-ray detectors arranged along the sectional direction in such a manner that all of said X-ray detectors can detect said X-ray beams extending along the sectional direction and passing through the biological body.

14. A method for reconstructing an X-ray CT (computerized tomographic) image of a biological body under medical examination, the method comprising the steps of:
acquiring continuous X-ray projection data of the biological body under medical examination by scanning both an X-ray source and an X-ray detector around the biological body in a helical scanning movement mode;
acquiring a plurality of cardiac beats of a heart of the biological body as electrocardiogram data;
converting temporal information contained in the electrocardiogram data into positional information of the biological body in connection with the helical scanning movement mode;
reconstructing a plurality of X-ray CT images by processing the continuous X-ray projection data based upon the positional information of the biological body, thereby producing the plurality of X-ray CT images having a specific relationship with phases of the cardiac beats of the heart; and
producing a three-dimensional image of the biological body by processing the plurality of reconstructed X-ray CT images having a specific relationship with phases of the cardiac beats of the heart, wherein said plurality of reconstructed X-ray CT images having a specific relationship with phases of the cardiac beats of the biological body are interpolated with each other to obtain one of an MPR (multi-planar reconstruction) image and a surface image of the biological body.

15. A method for reconstructing an X-ray CT (computerized tomographic) image of a biological body under medical examination, the method comprising the steps of:
acquiring continuous X-ray projection data of the biological body under medical examination by scanning both an X-ray source and an X-ray detector around the biological body in a helical scanning movement mode;
acquiring a plurality of cardiac beats of a heart of the biological body as electrocardiogram data;
converting temporal information contained in the electrocardiogram data into positional information of the biological body in connection with the helical scanning movement mode; and
reconstructing a plurality of X-ray CT images by processing the continuous X-ray projection data based upon the positional information of the biological body, thereby producing the plurality of X-ray CT images having a specific relationship with phases of the cardiac beats of the heart and each of said phases of the cardiac beats of the heart are selected to be a substantially central time instant within a cardiac expansion period.

16. An X-ray CT (computerized tomographic) imaging system comprising:
X-ray projection data acquiring means for acquiring continuous X-ray projection data about a biological body under medical examination, while scanning both an X-ray source and an X-ray detector around the biological body in a helical scanning movement mode;
electrocardiogram data acquiring means for acquiring a plurality of cardiac beats of a heart of the biological body as electrocardiogram data and the electrocardiogram data acquiring means selects substantially central time instants within cardiac expansion periods of the cardiac beats as selected phases of the cardiac beats;
converting means for converting temporal information contained in the electrocardiogram data into positional information of the biological body in connection with the helical scanning movement mode; and
reconstructing means for reconstructing a plurality of X-ray images by processing the continuous X-ray projection data based upon the positional information of the biological body, thereby producing the plurality of X-ray CT images having a specific relationship with the selected phases of the cardiac beats.

17. An X-ray CT (computerized tomographic) imaging system comprising:
X-ray projection data acquiring means for acquiring continuous X-ray projection data about a biological body under medical examination, while scanning both an X-ray source and an X-ray detector around the biological body in a helical scanning movement mode;
electrocardiogram data acquiring means for acquiring a plurality of cardiac beats of a heart of the biological body as electrocardiogram data;
converting means for converting temporal information contained in the electrocardiogram data into positional information of the biological body in connection with the helical scanning movement, the converting means includes at least a memory table for previously storing a conversion table by which the temporal information contained in the electrocardiogram data is converted into the positional information about the biological body in connection with the helical scanning movement mode; and
reconstructing means for reconstructing a plurality of X-ray images by processing the continuous X-ray projection data based upon the positional information of the biological body, thereby producing the plurality of X-ray CT images having a specific relationship with phases of the cardiac beats of the heart.

* * * * *

UNITED STATES PATENT AND TRADEMARK OFFICE
CERTIFICATE OF CORRECTION

PATENT NO. : 5,383,231
DATED : January 17, 1995
INVENTOR(S) : Ichiro YAMAGISHI

It is certified that error appears in the above-indentified patent and that said Letters Patent is hereby corrected as shown below:

Assignee, Title Page, Line 2 change "Kanegawa" to --Kanagawa--.

Attorney, Agent or Firm, Front Page, Line 2 change "Dunnar" to --Dunner--.

Claim 2, Column 8, Line 57 before "1" insert --claim--.

Claim 6, Column 9, Line 12 change "claim" (first occurrence) to --claimed--.

Signed and Sealed this

Sixth Day of June, 1995

BRUCE LEHMAN

*Attest:*

*Attesting Officer*   *Commissioner of Patents and Trademarks*